US012690785B2

(12) United States Patent
Grangeat et al.

(10) Patent No.: US 12,690,785 B2
(45) Date of Patent: Jul. 28, 2026

(54) PORTABLE DEVICE FOR ESTIMATING A GAS CONCENTRATION RELEASED BY A MEDIUM

(71) Applicants: Commissariat à l'Energie Atomique et aux Energies Alternatives, Paris (FR); L3 MEDICAL, Saint Quentin Fallavier (FR)

(72) Inventors: Pierre Grangeat, Grenoble cedex (FR); Myrna Violeta Jaillet-Casillas, Grenoble cedex (FR); Fabien Stocard, Sucy en Brie (FR)

(73) Assignees: Commissariat à l'Energie Atomique et aux Energies Alternatives, Paris (FR); L3 MEDICAL, Saint Quentin Fallavier (FR)

( * ) Notice: Subject to any disclaimer, the term of this patent is extended or adjusted under 35 U.S.C. 154(b) by 331 days.

(21) Appl. No.: 18/456,815

(22) Filed: Aug. 28, 2023

(65) Prior Publication Data

US 2024/0081695 A1      Mar. 14, 2024

(30) Foreign Application Priority Data

Aug. 28, 2022    (FR) ....................................... 2208591

(51) Int. Cl.
*A61B 5/1455* (2006.01)
*A61B 5/145* (2006.01)
(52) U.S. Cl.
CPC ...... *A61B 5/14542* (2013.01); *A61B 5/14552* (2013.01)
(58) Field of Classification Search
CPC .......................... A61B 5/1455; A61B 5/14542
See application file for complete search history.

(56) References Cited

U.S. PATENT DOCUMENTS

2014/0002823 A1    1/2014   Nakatani et al.
2022/0248992 A1    8/2022   Grangeat et al.

FOREIGN PATENT DOCUMENTS

JP          2010-148692 A     7/2010
WO      WO 2014/005931 A1    1/2014
                (Continued)

OTHER PUBLICATIONS

French Preliminary Search Report issued Jun. 27, 2023 in French Application 22 08591 filed on Aug. 28, 2022, 10 pages (with English Translation of Categories of Citied Documents and Written Opinion).

*Primary Examiner* — Marjan Fardanesh
(74) *Attorney, Agent, or Firm* — Oblon, McClelland, Maier & Neustadt, L.L.P.

(57) ABSTRACT

A measuring device is disposed against a medium, the device extending between a contact face applied facing the medium and a distal end, and including a lateral wall extending between the contact face and the distal end. The device includes: at the level of the contact face, an admission opening through the contact face collecting a transcutaneous gas of interest emitted through the medium; a measuring chamber including a gas sensor measuring a concentration of the gas of interest flowing through the measuring chamber; and a collecting chamber connected to the measuring chamber and delimited by an opening on the lateral wall, the collecting chamber including a lateral opening admitting a vector gas into the collecting chamber. The measuring chamber is disposed between the contact face and the collecting chamber. The device includes a pump driving a vector gas through the collecting chamber to an evacuation opening.

18 Claims, 8 Drawing Sheets

(56)  References Cited

FOREIGN PATENT DOCUMENTS

| WO | WO 2017/023500 A1 | 2/2017 |
| WO | WO 2020/249466 A1 | 12/2020 |

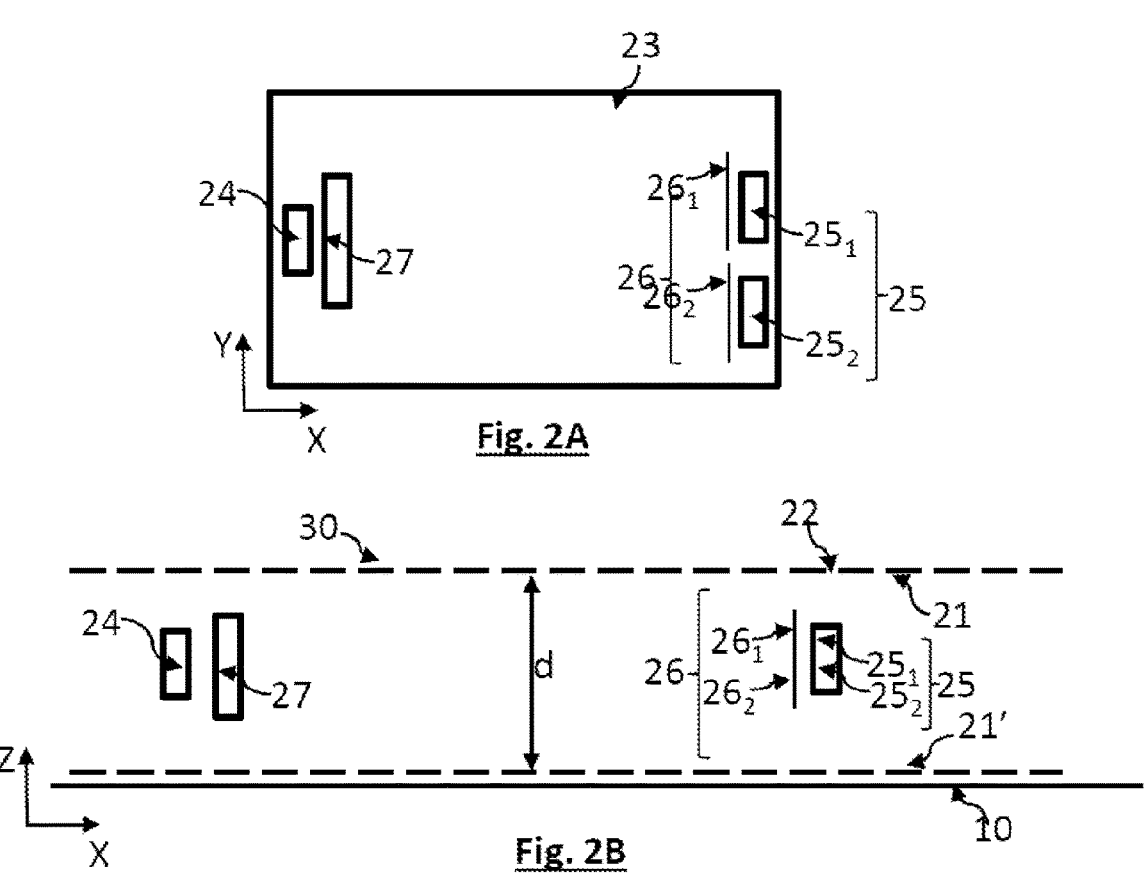
Fig. 2A
Fig. 2B
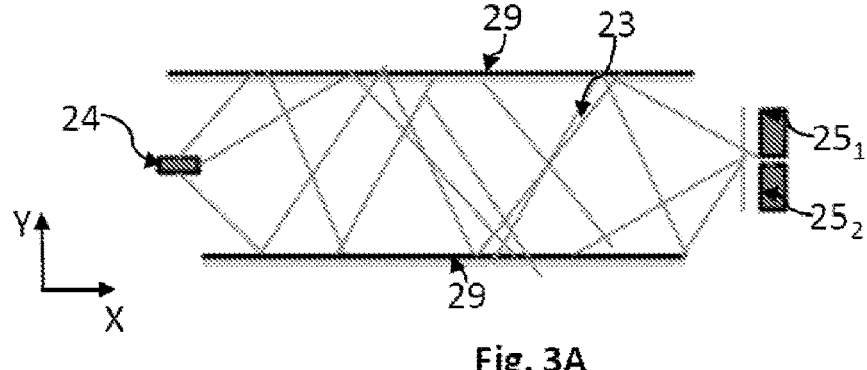
Fig. 3A
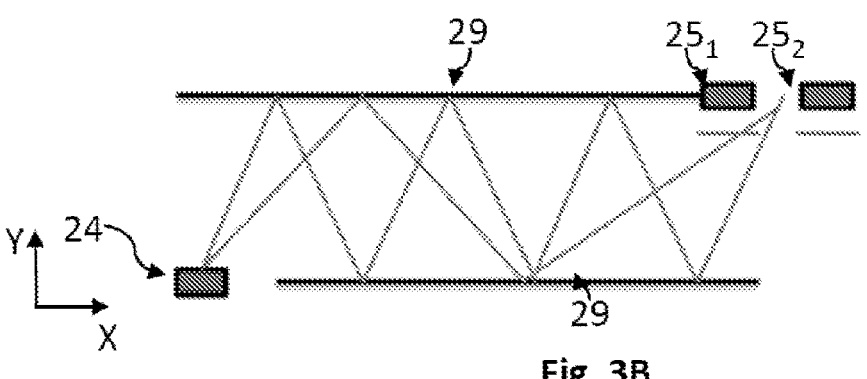
Fig. 3B

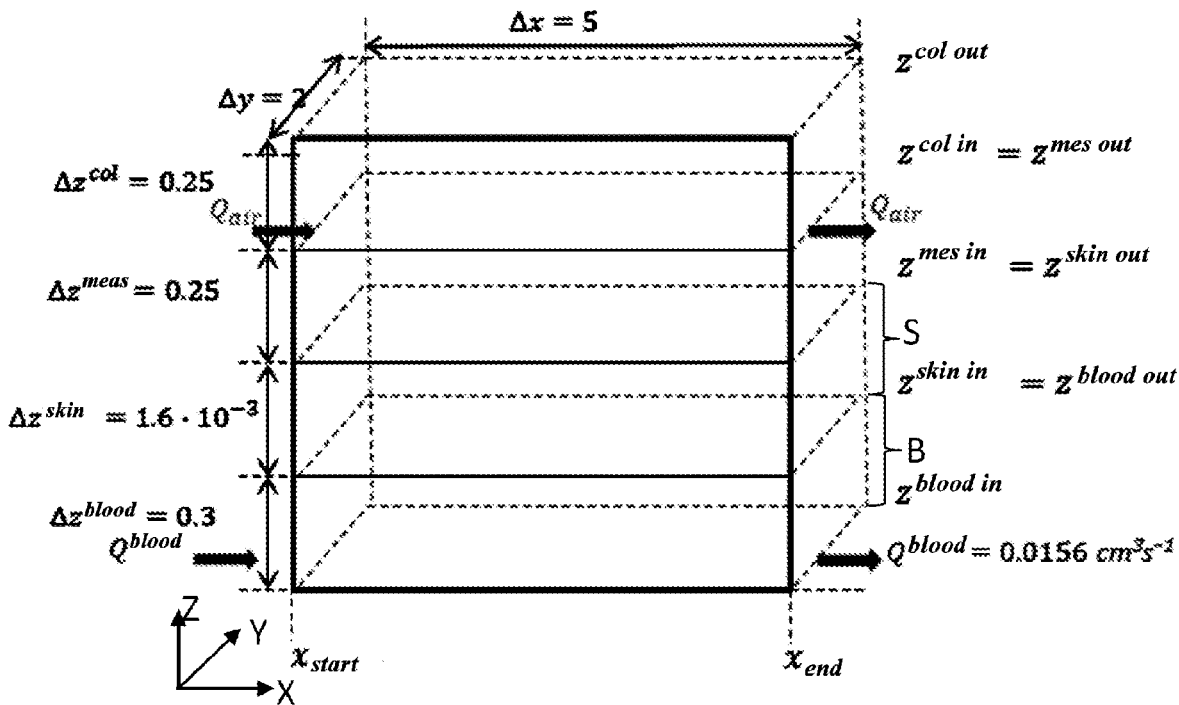
<u>Fig. 5C</u>

PORTABLE DEVICE FOR ESTIMATING A GAS CONCENTRATION RELEASED BY A MEDIUM

TECHNICAL FIELD

The technical field of the invention is the measurement of a gas given off by a medium using a compact device. The compact device is applied against the medium. The medium may be the skin of a living being. The device then enables estimation of physiological parameters, in particular the concentration of carbon dioxide dissolved in the blood. The gas may in particular be carbon dioxide, for capnometry applications. The medium may be a liquid medium, for example water or slurry. The gas may be carbon dioxide or methane. The medium may equally be a plant medium, in which case the device may be used to study the respiration of the medium.

PRIOR ART

Some respiratory illnesses affect the exchanges of gas between the blood and the expired air. The blood contains dissolved gases, including oxygen and carbon dioxide, the respective partial pressures of which reflect the exchanges of gases occurring at the level of the lungs and the organs.

To evaluate the quantity of $CO_2$ dissolved in the blood a blood sample may be used. This is an invasive method, which can be painful and difficult to use, in particular in neonatology. Moreover, it can be applied only in a localized manner. Despite these drawbacks its reliability is confirmed by the medical profession and it constitutes a reference method. Another method consists in estimating the concentration of $CO_2$ in the blood in a non-invasive manner, by effecting a measurement of the partial pressure of $CO_2$ diffusing through the tissues and in particular the skin. This method is known as transcutaneous capnometry.

The carbon dioxide in the blood is dissolved in the form of one molecular species ($CO_2$) and two ionic species: carbonate ions $CO_3^{2-}$ and bicarbonate ions $HCO_3^-$. The balance between these species depends on the pH of the blood. The carbonate and bicarbonate ions are in equilibrium with the hydrogen ions. The concentration of carbonate or bicarbonate ions therefore influences the pH of the blood. An increase in the concentration of dissolved $CO_2$ (hypercapnia) is reflected in an increase in the quantity of carbonate and bicarbonate ions and, through equilibrium, hydrogen ions, which generates a reduction of the pH of the blood also known as acidosis. An increase in the concentration of $CO_2$ can occur if the elimination of the $CO_2$ via the respiratory channels is insufficient, for example in the case of chronic obstructive pulmonary disease (COPD) or an infectious disease affecting the lungs, one example being infection caused by COVID 19.

Conversely, a decrease in the concentration of dissolved $CO_2$ (hypocapnia) lowers the concentration of hydrogen ions, which leads to an increase in the pH, also known as alkalosis. Hypocapnia can be caused for example by hyperventilation associated with an increase in the respiratory frequency. The onset of acidosis or alkalosis can have consequences for the metabolism. Thus the concentration of $CO_2$ in the blood is a vitally important parameter that has to be monitored regularly for some patients.

Monitoring the concentration of $CO_2$ may equally concern patients being resuscitated or neonates in an incubator. It can also find applications in monitoring effort, physical activity favoring the production of carbon dioxide.

This type of transcutaneous analysis was introduced in the 1980s. Transcutaneous analysis enables continuous monitoring, for example to monitor the immediate effects of therapeutic action. It can also enable determination of the times at which a precise quantification, by taking a blood sample, is necessary. It is therefore clear that invasive and non-invasive methods may be combined: one is precise and localized, whereas the other may be carried out continuously.

A compact device enabling transcutaneous $CO_2$ measurement has already been described in WO2020/249466. This is a non-invasive measuring device worn by a user to estimate a concentration of a gas of interest emitted transcutaneously, the gas of interest being carbon dioxide, for example. Circulation of the gas of interest in the device enables collection of the gas. The transcutaneous gas of interest is propagated through the device by convection, because of the effect of a heat source. The device includes a contact face intended to be applied against the user. The device equally includes a measuring chamber including a $CO_2$ sensor. For the increase in temperature to be reflected in convection, it is preferable for the measuring chamber to be disposed above the contact face.

The inventors are proposing an improvement to be device described in WO2020/249466 aimed at improving certain aspects of performance, in particular response time.

STATEMENT OF INVENTION

A first object of the invention is a measuring device intended to be disposed against a medium, the device extending between a contact face intended to be applied facing the medium and a distal end, the device including a lateral wall extending between the contact face and the distal end, the device including:

at the level of the contact face, at least one admission opening configured to collect a gas of interest emitted through the medium, the admission opening being through the contact face;

a measuring chamber including a gas sensor, the gas sensor being configured to measure a concentration of the gas of interest flowing through the measuring chamber;

a collecting chamber connected to the measuring chamber and delimited by an opening on the lateral wall, the collecting chamber including at least one lateral opening through the lateral face so as to admit a vector gas into the collecting chamber;

the device being characterized in that:

the measuring chamber is disposed between the contact face and the collecting chamber;

the device includes a driving means configured to drive the vector gas through the collecting chamber to an evacuation opening so that driving the vector gas induces transport of the gas of interest from the contact face to the collecting chamber via the measuring chamber.

The driving means may blow or suck air. The gas of interest is transported from the contact face to the collecting chamber, via the measuring chamber by diffusion. Diffusion is favored by a reduced pressure formed in the measuring chamber by the driving means.

The device may include a heat source configured to heat the contact face to a temperature greater than 37° C.

In accordance with one embodiment the evacuation opening is oriented about an evacuation axis perpendicular or perpendicular to within 30° to the contact face, the collecting chamber opening into the evacuation opening.

In accordance with one embodiment the evacuation opening is through the lateral wall of the collecting chamber.

In accordance with one possibility the gas sensor of the measuring chamber is disposed at a distance less than 8 mm from the contact face.

The gas sensor may be an optical sensor including an infrared light source configured to emit infrared light and a photo detector, the measuring chamber being such that the gas of interest flows in the measuring chamber between the source of infrared light and the photodetector in a flow direction perpendicular or perpendicular to within ±30° to the contact face. The source of infrared radiation may be configured to produce a flat light beam parallel or parallel to within ±30° to the contact face. The thickness of the flat light beam in the direction of a transverse axis perpendicular to the contact face is less than 5 mm.

The measuring chamber may include two walls parallel to the contact face, each wall being reflective to the infrared light emitted by the infrared source, the walls delimiting a flat light beam in which the infrared light propagates between the infrared source and the photodetector. A reflecting wall forms the contact face.

The reflecting wall nearest the contact face may configured to be heated so as to heat the medium.

The device may be such that:

each reflecting wall includes transverse baffles;

each transverse baffle of a reflective wall extends toward an opposite reflective wall;

a gap is formed between each transverse baffle and the reflective wall opposite it;

a transverse baffle of a reflective wall extends between two transverse baffles of the opposite reflective wall;

so that the light emitted by the light source propagates between the successive transverse baffles before reaching the detector The pump air flowrate may be between 0.1 and 10 mL/min.

Another object of the invention is a method of estimating a concentration of a gas of interest in a medium using a device conforming to the first aspect of the invention, the device being applied so that the contact face is disposed facing the medium, the vector gas driving means being activated, the method including:

a) estimating a gas of interest concentration in the measuring chamber;

b) from the gas of interest concentration in the measuring chamber resulting from step a) estimating a partial pressure of the gas of interest given off by the medium.

The medium may be the skin of a user, the skin extending over a blood vessel, in which case step b) includes:

(i) on the basis of the gas of interest concentration in the measuring chamber resulting from step a) estimating a transcutaneous gas of interest concentration;

(ii) estimating a concentration or partial pressure of the gas of interest dissolved in the medium on the basis of the transcutaneous gas of interest concentration resulting from sub-step (i).

The medium to be analyzed may be a solid or liquid medium. The vector gas may be air.

The invention will be better understood on reading the description of embodiments of the invention given in the remainder of the description with reference to the figures listed below.

FIGURES

FIG. 2A is a diagram of the main components of a gas sensor disposed in the measuring chamber of the device, as seen in a plane perpendicular to a transverse axis.

FIG. 2B is a diagram of the main components of a gas sensor based on absorption of infrared light disposed in the measuring chamber of the device, as seen in a plane parallel to the transverse axis passing through the infrared light source 24 and the infrared light detector 25.

FIGS. 3A, 3B, 3C and 3D show different configurations of a gas sensor.

FIGS. 5A, 5B and 5C are diagrams respectively showing a prior art configuration, a configuration in accordance with a first embodiment of the invention and a configuration in accordance with a second embodiment of the invention.

DESCRIPTION OF PARTICULAR EMBODIMENTS

Figures 1A, 1B:
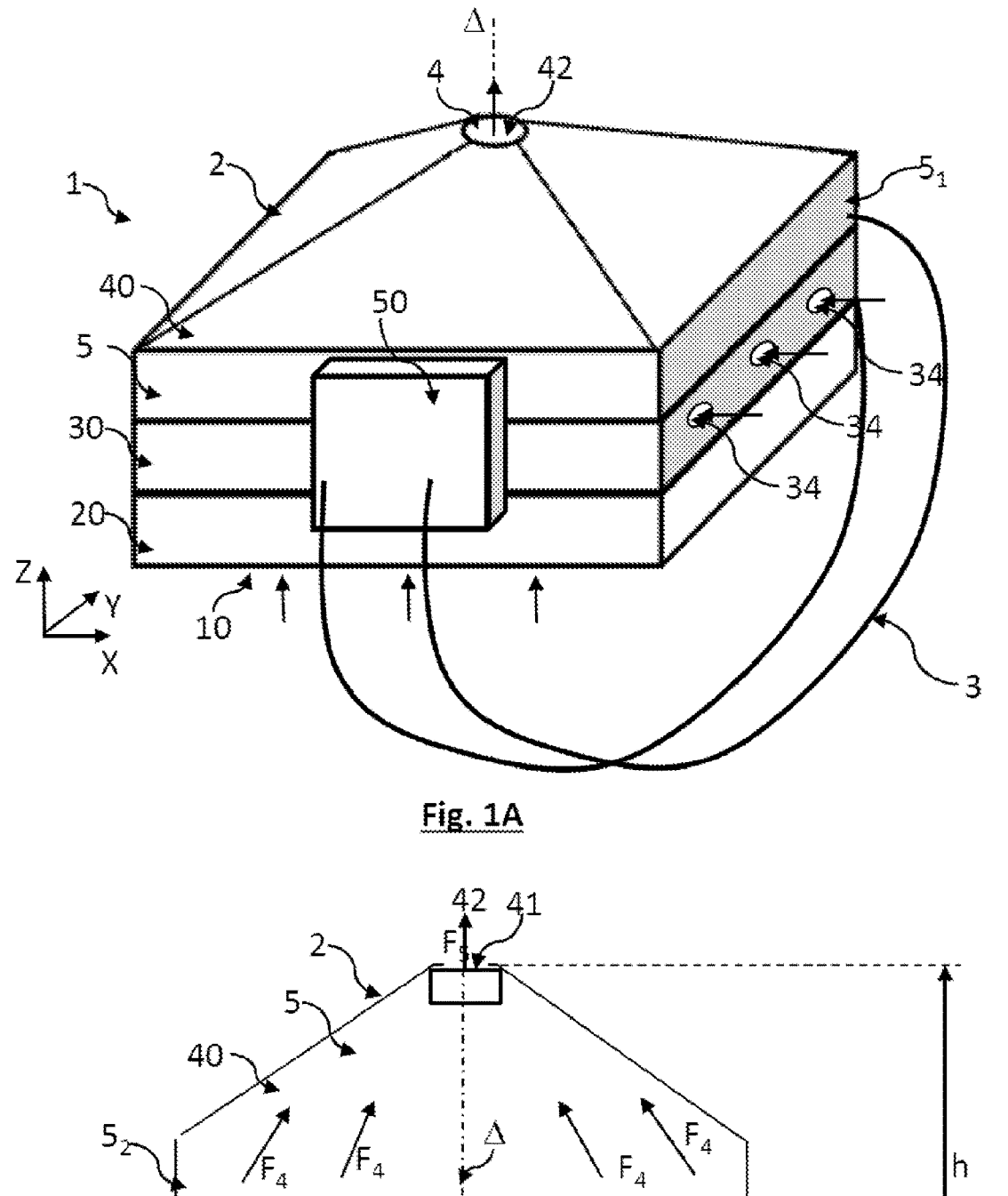
FIG. 1A shows a first embodiment of a device according to the invention.
FIG. 1B is a diagram of the flows inside the device.

FIGS. 1A and 1B are general views of one example of a device 1 according to the invention. The device 1 is intended to be disposed in contact with a medium that it is wished to analyze. In the example described the medium is the skin S of a human user or an animal. The device includes a main body 2 and a fixing element 3, a bracelet in this example. Alternatively, the main body may be disposed in contact with an earlobe or a finger. The support may be a clamp or integrated into a headset. More generally, the support is configured to hold the main body in contact with the medium to be analyzed.

The device is intended to estimate a concentration of a gas of interest emanating from the skin of a user. By gas of interest is meant a gas a concentration of which in a living animal or human body it is wished to determine, more particularly in the blood of the latter. In the example described hereinafter in a non-limitative manner the gas of interest is carbon dioxide, a concentration of which in the blood of the user it is sought to estimate. In accordance with other possibilities the gas of interest may be, in a non-limitative manner, oxygen, ethyl alcohol, carbon monoxide, methane, nitrogen monoxide, acetone or isoprene, hydrogen, some drugs or volatile substances.

The main body 2 has a contact face 10 intended to be applied to the skin S. The contact face 10 is substantially planar, in the sense that it extends parallel to a plane XY, some portions possibly being inclined relative to the plane XY. The main body also has a distal end 4 opposite the contact face 10. The contact surface 10 and the distal end 4 are connected to one another by a lateral face 5 extending around a central axis Δ parallel to a transverse axis Z perpendicular to the plane XY.

The contact face 10 may be formed by a membrane permeable to $CO_2$ or a plate including admission openings 12 enabling $CO_2$ to pass through it. The contact face may include a hydrophobic membrane so as to prevent the diffusion of water vapor through the device 1.

In accordance with one possibility the device equally includes a heating element enabling the contact face 10 delimiting the measuring chamber 20 to be heated to a temperature greater than 37° C., preferably between 40° C. and 50° C. inclusive, preferably between 40° C. and 45° C., for example 42° C. The heating element is for example a resistive element on the contact face producing heat by the Joule effect. A local and moderate increase in temperature in the vicinity of the skin favors an increase in the blood flowrate by expansion of the blood capillaries, which increases the transcutaneous diffusion of a gas of interest through the skin.

The contact face 10 opens into a measuring chamber 20. The function of the measuring chamber is to estimate a $CO_2$ concentration of the gas mixture circulating in the main body 2 parallel or substantially parallel to the central axis Δ. To this end the measuring chamber 20 includes a gas sensor 23. A number of sensor types may be used for this purpose, for example optical sensors or electrochemical sensors, the latter in particular possibly being based on metal oxides (MOX sensors), or photo-acoustic sensors. The optical sensor may be a fluorescent sensor. The inventors have deemed it preferable to use an optical sensor and to be more precise an infrared sensor. A sensor of this kind does not necessitate any particular maintenance and is particularly compact, as well as of relatively low cost. Furthermore, a sensor of this kind is highly specific for characterizing chemical bonds. It is suitable for the detection of molecules of small size, for example carbon dioxide molecules.

The gas sensor is a non-dispersive infrared (NDIR) type sensor. This type of sensor includes a source 24 of infrared radiation, generally emitting in a spectral band between 1 μm and 20 μm inclusive. It equally includes at least one measurement photodetector 25 sensitive to infrared radiation. The operating principle is based on attenuation by the analyzed gas of the infrared radiation emitted by the source. The infrared source 24 and the measurement photodetector 25 form the gas sensor 23. The measurement photodetector 25 is for example a thermopile. A filter 26 placed in front of the thermopile determines the wavelength of the infrared radiation measured by the thermopile. Different configurations of the gas sensor are described hereinafter.

The gas sensor 23 is configured so that the transcutaneous gas of interest, here $CO_2$, propagates between the light source and the photodetector, parallel to the central axis Δ or substantially parallel to the central axis Δ. By substantially parallel is meant parallel to within an angular tolerance of less than ±30° or ±20°.

The infrared source emits light propagating perpendicularly to the transverse axis Z. The light emitted by the source if preferably a flat light beam perpendicular to the transverse axis Z. The thickness of the beam in the direction of the transverse axis Z is preferably less than 1 cm, preferably less than 5 mm. The flat light beam preferably extends over at least 50% or even at least 80% of the cross section of the contact face 10, the latter being between a few $cm^2$ and 25 or 30 $cm^2$ inclusive. By cross section is meant a surface perpendicular to the transverse axis Z (or to the central axis Δ). The small thickness of the beam enables the response time to be reduced. The large area of the cross section of the beam enables the quantity of gas sampled and therefore the sensitivity of the measurement to be increased.

In order to favor flow along the transverse axis Z through the measuring chamber 20 the contact face includes a multitude of admission openings 12 distributed across a cross section of a few $cm^2$, for example between 5 and 25 $cm^2$. The admission openings form a transparency factor $r_{meas\_trans}$. The transparency factor corresponds to the area of the admission openings on the surface of the contact face. This corresponds to a proportion of the contact face opening onto the medium to be analyzed. Alternatively, the contact face supports a porous membrane that is permeable to $CO_2$. The measuring chamber 20 opens into a collecting chamber 30. The interface between the measuring chamber 20 and the collecting chamber 30 may be formed by a wide collecting opening or by a plurality of collecting openings 22 in a collecting plate 21 and distributed across a cross section of large area, in a similar manner to the admission openings 12. Each collecting opening 22 opens into a collecting chamber 30.

The collecting chamber 30 includes lateral openings 34 in the lateral face 5 of the device 1. The lateral openings are configured to enable admission of ambient air into the device 1. Ambient air is the air situated outside the device. The flow of ambient air through the lateral openings 34 is directed toward the central axis Δ. Each lateral opening 34 is preferably oriented perpendicularly to the central axis Δ so that the ambient air penetrates into the device 1 through each lateral opening 34 in a direction perpendicular or substantially perpendicular to the central axis Δ.

The admission of ambient air is achieved by means of a pump 41 adapted to create transport of the carbon dioxide in the collecting chamber by convection and the vector gas may be ambient air or possibly another vector gas such as nitrogen. Ambient air is introduced via the lateral openings and driven across the collecting chamber to an evacuation opening. The pump 41 may be situated in an evacuation pipe 40 adjacent to the collecting chamber 30. Evacuation of the gas of interest by the vector gas impoverishes the gas of interest content of the collecting chamber and reduces its partial pressure. The gas of interest partial pressure difference between the face in contact with the skin and the collecting chamber induces flow by diffusion of the gas of interest across the measuring chamber 10 to the collecting chamber 20 via the admission openings 12 and the collecting openings 22. The flowrate of the vector gas in the collecting chamber is preferably adjusted so that the flow by diffusion of the gas of interest across the measuring chamber 20 is laminar flow. The flowrate of the vector gas in the collecting chamber can for example be between 0.1 and 10 mL/min, depending on the volume of the chamber.

In the collecting chamber 30 ambient air admitted via the lateral openings 34 is mixed with the gas of interest admitted via the collecting openings 22. The air mixed with the gas of interest is evacuated by convection in the evacuation pipe to an evacuation opening 42 forming the distal end 4 of the device. In the example represented in FIGS. 1A and 1B the air propagates through the evacuation opening 42 around the central axis Δ. In accordance with another possibility described with reference to FIGS. 6A and 6B the air is propagated through the evacuation opening 42 along an evacuation axis Δ' intersecting, and in particular perpendicular to, the central axis Δ.

In the example represented the lateral openings are disposed on two opposite faces $5_1$, $5_2$ of the lateral wall. This favors symmetry of the flow of air in the device. However, a symmetrical arrangement of this kind of the lateral openings is not necessary. The lateral openings 34 may be on a face of the lateral wall, the evacuation pipe then being disposed on an opposite face of the lateral wall. See for example the embodiment represented in FIG. 6A.

Each lateral opening may be associated with a filter trapping the gas of interest. In this example this is a $CO_2$ filter, for example a filter including lime so as to trap the $CO_2$ present in the ambient air.

The device includes a processing unit 50. The processing unit 50 includes calculation means, for example a microprocessor or a microcontroller, onboard the device, connected by a wired or wireless connection to a mobile telephone or a PC type computer. The processing unit 50 is equally configured to execute the method for estimating the concentration of dissolved $CO_2$ in the blood of the user based on the $CO_2$ concentration from the gas sensor 23.

The general principles governing estimation of the dissolved $CO_2$ concentration in the blood from the $CO_2$ concentration detected in the gas sensor have been described in WO2020/249466.

The method includes calculation of the concentration of the carbon dioxide in the measuring chamber based on measurements carried out by the two thermopiles based on models describing the attenuation of the infrared radiation at the two wavelengths associated with each of the thermopiles (Beer Lambert model, linear quadratic model). These models are described in WO2020/249466.

The resulting measurements from the sensor may be accompanied by noise, in which case low-pass filtering may be applied. The low-pass filtering may for example be performed by a sliding mean filter the length of which is adapted to the level of measurement noise.

The concentration of CO2 in the blood may be estimated using the expression $$C_{CO_2}^{blood\ in} = H^{blood} C_{CO_2}^{col\ in} +$$

$$\frac{Q^{air} + r_{meas\_trasp} A^{blood} K^{meas-skin-blood} H^{blood}}{r_{meas\_transp} A^{blood} K^{meas-skin-blood}} \cdot \left[ C_{CO_2}^{meas\ out} - C_{CO_2}^{air\ col\ in} \right]$$

where:

$$C_{CO_2}^{blood\ in}$$

is the concentration of the carbon dioxide in the blood at the inlet of the blood compartment;

$$C_{CO_2}^{air\ col\ in}$$

is the concentration of the carbon dioxide in the ambient air at the inlet of the collecting chamber. This concentration can be measured by an auxiliary sensor intended to determine the $CO_2$ concentration in the ambient air around the device, as described in WO2020/249466. In accordance with another feature, a filter absorbing $CO_2$ is disposed at the level of the lateral openings 34. In this case it is assumed that $$C_{CO_2}^{air\ col\ in} = 0;$$

$$C_{CO_2}^{mess\ out}$$

is the concentration of the carbon dioxide in the measuring chamber;

$Q^{air}$ is the flowrate of air in the collecting chamber;

$A^{blood}$ is the area of contact between the device and the skin;

$K^{meas-skin-blood}$ is the total mass transfer coefficient through the blood, skin and measuring chamber;

$H^{blood}$ is the Henry coefficient defining the solubility of the carbon dioxide in the blood;

$r_{meas\_transp}$ is the transparency factor of the grille between the skin and the measuring cell;

The pressure $$P_{CO_2}^{blood\ in}$$

in of the $CO_2$ in the blood is deduced from this on the basis of the concentration of $$C_{CO_2}^{blood\ in}$$

$$P_{CO_2}^{blood\ in} = \frac{C_{CO_2}^{blood\ in}}{\beta^{blood}}$$

where:

$\beta^{blood}$ is the Ostwald solubility coefficient of the carbon dioxide in the blood.

FIG. 1B is a diagram of the fluidic currents formed inside the device 1. The transcutaneous $CO_2$ is admitted into the device via the admission openings 12 in the contact face 10 and opening into the measuring chamber 20 (cf. arrow $F_1$). The $CO_2$ propagates across the measuring chamber by diffusion, parallel to the central axis, the latter being parallel to the transfer axis Z. (cf. arrows $F_2$). The ambient air is admitted via the lateral openings 34 in the lateral wall (cf. arrows $F_3$). The gas mixture including the ambient air and the transcutaneous $CO_2$ is produced in the collecting chamber 30. This mixture propagates to the evacuation opening 42 (cf. arrows $F_4$) to exit the body 2 of the device (cf. arrows $F_5$).

An important aspect of the device is the use of the pump 41, which enables a current of air to be formed at the level of the collecting chamber 30 to evacuate the air/transcutaneous gas of interest mixture to be evacuated. This also enables acceleration of the circulation of air in the collecting chamber. This results in a pumping effect accelerating the diffusion of the $CO_2$ from the blood to the air via the skin and the measuring chamber. This results in a reduction of the response time of the device. If the medium to be analyzed undergoes a step increase in the $CO_2$ concentration the response time of the detector corresponds to a rise time. The rise time corresponds to the time to produce between 10% and 90% of the variation in the concentration of the carbon dioxide in the measuring chamber after application of the step. It may be estimated using the following approximate formula:

$$\Delta t^{rise} = 2.198 \cdot \tau =$$

$$2.197 \cdot \frac{1}{\frac{r_{meas\_transp} A^{blood}}{V^{col} + V^{meas}}} \cdot \frac{1}{\frac{Q^{air}}{r_{meas\_transp} A^{blood}} + K^{meas-skin-blood} H^{blood}}$$

where:

$Q^{air}$ is the flowrate of air in the collecting chamber;

$A^{blood}$ is the area of contact between the device and the skin;

$K^{meas\text{-}skin\text{-}blood}$ is the total mass transfer coefficient through the blood, skin and measuring chamber;

$H^{blood}$ is the dimensionless Henry coefficient defining the solubility of the carbon dioxide in the blood;

$V^{meas}$ is the volume of the measuring chamber;

$V^{col}$ is the volume of the collecting chamber;

$r_{meas\_transp}$ is the transparency factor of the area of contact between the skin and the measuring cell. The transparency factor corresponds to the proportion of the contact area that is open: this is the ratio between the area of the part of the contact face open onto the medium to be analyzed (here the skin of the user), thus allowing the gas to pass, to the total area of the contact face.

It is considered that the main body has a parallelepipedal geometry with the surface to volume ratio $$\frac{A^{blood}}{V^{col} + V^{meas}}$$

being:

$$\frac{A^{blood}}{V^{col} + V^{meas}} = \frac{1}{\Delta z^{col} + \Delta z^{meas}}$$

where:

$\Delta z^{col}$ is the height of the collecting chamber, $\Delta z^{meas}$ is the height of the measuring chamber.

The smaller these heights $\Delta z^{col}$ and $\Delta z^{meas}$, the greater the area-to-volume ratio $$\frac{A^{blood}}{V^{col} + V^{meas}}$$

and the shorter the rise time.

This expression also shows the importance of the transparency factor. The closer it is to 1, the shorter the rise time.

As indicated above, the height over which the measuring chamber extends between the admission openings 12 and the collecting openings 22 is relatively small, preferably less than 5 mm, more preferably 3 mm. The same applies to the collecting chamber.

More generally, the device has a high area-to-volume ratio. The height h between the contact face 10 and the upper face of the collecting chamber is therefore preferably less than 15 mm, more preferably 8 mm.

Another important aspect of the invention is minimizing the distance between the measuring chamber 20 and the contact face 10. This enables measurement of the $CO_2$ as close as possible to the skin. This is an important difference compared to the device described in the prior art, in which a collecting chamber including lateral openings extends between the contact face and the measuring chamber. Moving the measuring chamber 20 closer to the skin enables the response time of the device to be improved.

FIG. 2A is a diagram of the measuring chamber 20 in a plane $P_{XY}$ perpendicular to the transverse axis. It defines a measuring volume extending between a source 24 of infrared radiation and the measuring photodetector 25. The source and the detector are components of the $CO_2$ sensor 23.

The photodetector 25 includes a measuring channel $25_1$ and a reference channel $25_2$. The measuring channel $25_1$ is configured to detect the radiation propagated across the measuring chamber 20 in an absorption spectral band that corresponds to the gaseous species that it is wished to analyze, here $CO_2$. The measuring channel $25_1$ therefore measures the intensity of the radiation transmitted by the gas mixture in a detection spectral band centered on $\lambda_1 = 4.26$ μm, defined by a measuring filter $26_1$. The reference channel $25_2$ is configured to detect the radiation that has propagated across the measuring chamber 20 in a reference spectral band in which absorption by the gas mixture is considered negligible. The reference spectral band is for example centered on $\lambda_2 = 3.91$ μm. It is defined by a reference filter $26_2$. Note that at the detection wavelength $\lambda_1$ and at the reference wavelength $\lambda_2$ the absorption of the radiation by water vapor may be considered equal. Failing this, the moisture concentration is taken into account in the model, as described hereinafter. The same applies to the absorption of air, which may be considered equal at both wavelengths.

To widen the beam in a plane perpendicular to the transverse axis the infrared source 24 may be coupled to a diffuser 27.

The measuring chamber 20 preferably includes a temperature sensor, a moisture sensor and a pressure sensor.

The temperature sensor converts the measured concentration in terms of pressure in accordance with the perfect gas law. Using the perfect gas law, there is deduced therefrom the partial pressure $$P_{CO_2}^{meas}(T^{meas})$$

of the carbon dioxide in the measuring chamber at the temperature $T^{meas}$:

$$P_{CO_2}^{meas}(T^{meas}) = C_{CO_2}^{meas} \cdot R \cdot T^{meas}$$

where $$C_{CO_2}^{meas} \text{ is}$$

is expressed in (mol/m³), R is the perfect gas constant (0.0623637 m³·mmHg·K⁻¹·mol⁻¹), $T^{meas}$ in K and $$P_{CO_2}^{meas}$$

in mmHg.

The sensor of atmospheric pressure $$P_{air}^{meas}$$

is used to calculate the relative pressure $$P_{CO_2}^{meas\ rel}$$

expressed in ppm (parts per million):

$$P_{CO_2}^{meas\ rel} = \frac{P_{CO_2}^{meas}}{P_{air}^{meas}} \cdot 10^6$$

where $$P_{CO_2}^{meas}\ et\ P_{air}^{meas}$$

are expressed in the same unit, here in mmHg.

The moisture sensor is used to calculate the concentration of water vapor in the measuring chamber. Water vapor is associated with a high radiation attenuation factor. Taking moisture into account necessitates conversion of the relative humidity value $RH^{meas}$ supplied by the humidity sensor into a water vapor concentration $$C_{H_2O}^{meas}$$

The relative humidity corresponds to the partial pressure of water in the measuring chamber, denoted $$P_{H_2O}^{meas}(T^{meas})$$

referred to the saturated vapor pressure at the temperature $T^{meas}$ of the measuring chamber.

$$RH^{meas} \triangleq \frac{P_{H_2O}^{meas}}{VP_{H2O}(T^{mas})} \cdot 100\%$$

The $H_2O$ concentration in the measuring chamber may be obtained using the expression:

$$P_{H_2O}^{meas} = C_{H_2O}^{meas}.R.T^{meas}$$

Combining the above two equations:

$$C_{H_2O}^{meas} = \frac{RH^{meas} \cdot VP_{H2O}(T^{meas}).}{100\% R \cdot T^{meas}}$$

The saturated vapor pressure values $VP_{H2O}(T^{meas})$ as a function of temperature may be obtained from tables or from an analytic expression, for example the Tetens equation:

$$VP_{H2O}(T^{meas}) = 0.61078e^{\left(\frac{17.27(T^{meas}-273.15)}{T^{meas}-35.85}\right)}$$

The concentration $$C_{H_2O}^{meas}$$

may be used to estimate the $CO_2$ concentration in the measuring chamber using the Beer-Lambert expression:

$$-\ln\left[\frac{U(\lambda_1)/U(\lambda_2)}{U_0(\lambda_1)/U_0(\lambda_2)}\right] = \left[k_{CO_2}(\lambda_1) - k_{CO_2}(\lambda_2)\right] \cdot$$
$$C_{CO_2} + \left[k_{H_2O}(\lambda_1) - k_{H_2O}(\lambda_2)\right] \cdot C_{H_2O} + [A_{air}(\lambda_1) - A_{air}(\lambda_2)]$$

where $C_{CO_2}$ and $C_{H_2O}$ are the molar concentrations $k_{CO_2}(\lambda_1)$, $k_{CO_2}(\lambda_2)$, $k_{H_2O}(\lambda_1)$, $k_{H_2O}(\lambda_2)$, the attenuation coefficients of the carbon dioxide and of the water vapor $A_{air}(\lambda_1)$, $A_{air}(\lambda_2)$, the attenuation coefficients of the air at the wavelengths $\lambda_1$, $\lambda_2$.

Taking account of the $H_2O$ concentration therefore enables the precision with which the $CO_2$ concentration is measured to be improved, as mentioned in the patent application WO2020/249466.

FIG. 2B shows the measuring chamber in a plane $P_{XZ}$ parallel to the transverse axis Z. The measuring chamber may extend between two grilles 21 and 21' permeable to the gas of interest. The grille 21 forms the interface wall with the collecting chamber 30. It includes collecting openings enabling the gas of interest to flow from the measuring chamber to the collecting chamber. Each grille is preferably reflective in the emission spectral band of the infrared source. The measuring chamber may include a reflective grille 21' similar to the grille 21 at the level of the contact face 10. The presence of each reflective grille enables the quantity of light propagating through the gas of interest to each channel of the photodetector to be increased. This equally enables limitation of the thickness of the flat light beam in the direction of the transverse axis.

The distance d between the grille 21 and the contact face or between the grilles 21 and 21' is for example between 3 mm and 8 mm inclusive.

Figure 3C:
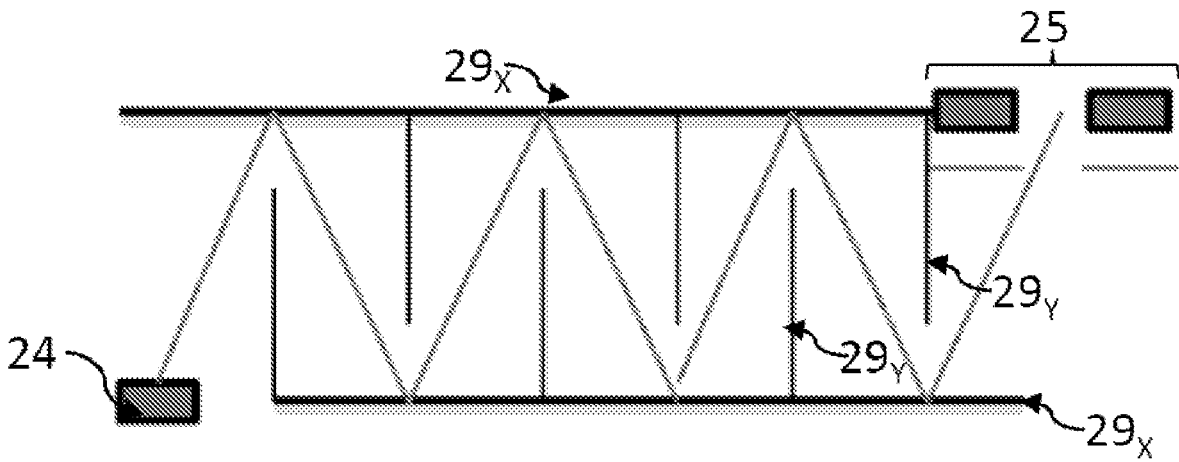

FIGS. 3A to 3D depict different arrangements of the gas sensor 23 enabling a thin flat light beam extending perpendicularly to the transverse axis Z to be formed. In the direction of the lateral axis Y the dimension of the flat beam is limited by reflective walls 29. In FIGS. 3A and 3B the infrared source emits in the direction of the longitudinal axis X and the lateral axis Y. In FIG. 3C the infrared source emits through reflective walls arranged as interleaved combs. Each reflective wall 29 has a longitudinal section $29_X$ extending along the longitudinal axis X from which project a plurality of transverse baffles $29_Y$ parallel to the lateral axis Y. The walls are disposed face to face so that a transverse baffle of one wall extends between two adjacent transverse baffles of the opposite wall. Each transverse baffle does not reach the longitudinal section opposite it: a gap is left free between each transverse baffle and the longitudinal section opposite it. The gap allows passage of light between the end of each transverse baffle and the opposite longitudinal section. The light propagates successively between each transverse baffle and the opposite longitudinal section. The transverse baffles are termed interlaced or interleaved. This configuration enables the optical path to be lengthened compared to a direct path along the axis X, while ensuring less spread over the length of the optical paths of the rays emitted by the light source and detected by each measuring channel. The light emitted by the light source therefore propagates between the walls along the channels delimited by the transverse portions.

Figure 3D:
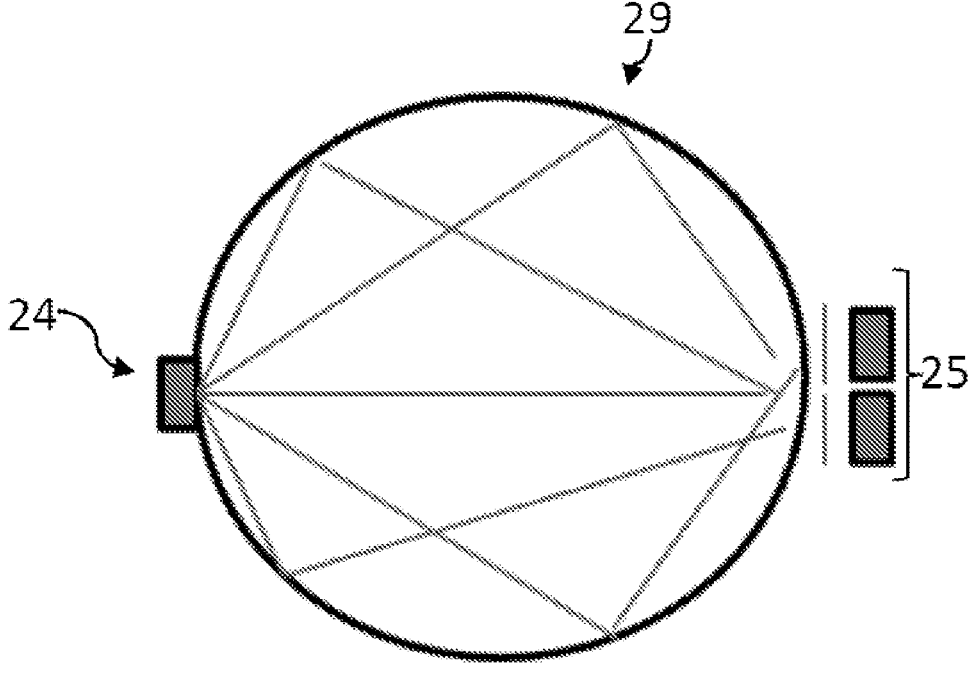

In FIG. 3D the flat light beam is delimited by a circular reflective wall enabling all paths between the source and the thermopile in diametrally opposite positions to be the same length.

Figure 4A:
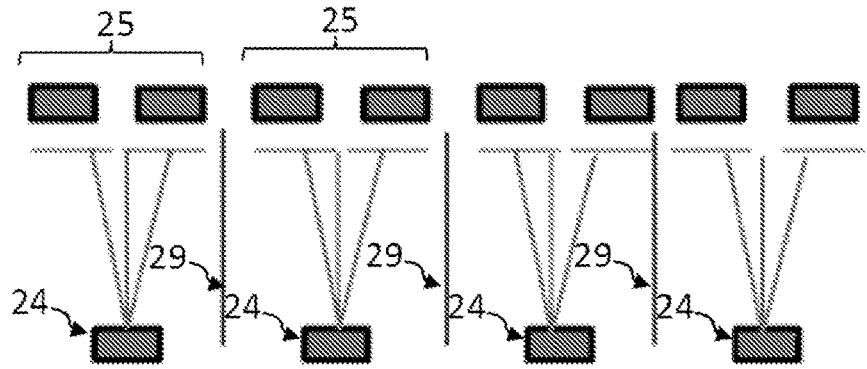
FIGS. 4A, 4B and 4C show different configurations of a gas sensor including a plurality of infrared light sources.
Figure 4B:
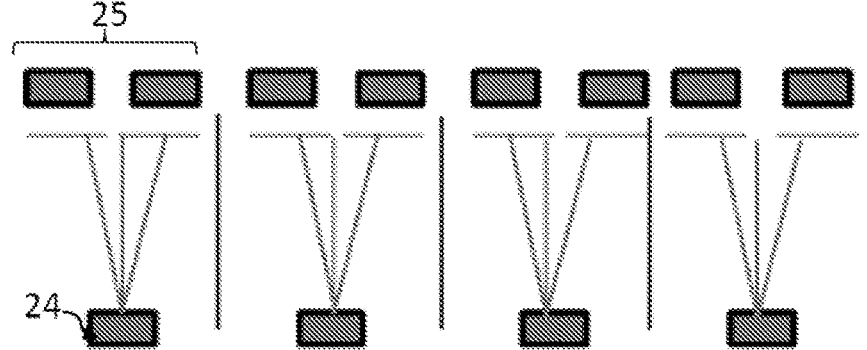
Figure 4C:
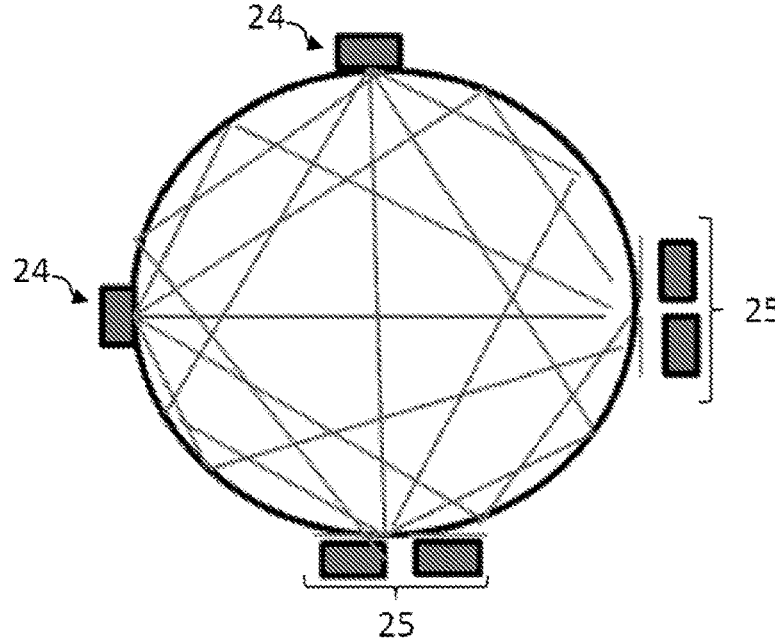

FIGS. 4A to 4C represent configurations in which a plurality of assemblies are available to render the measurements parallel and to improve the sensitivity of the device. Each assembly includes a light source and a photodetector including two measuring channels, as described above. In the configuration represented in FIG. 4A the assemblies are separated from one another by a reflective wall 29. This enables less spread of the optical paths of the rays emitted by the light source and detected by each measuring channel. In FIG. 4B no reflective wall is used in order to increase the quantity of light received by each thermopile and to increase sensitivity. This is achieved to the detriment of the non-linearity introduced by spread over the length of the optical paths depending on the positioning of the source and the thermopile. In FIG. 4C the flat light beam is delimited by a circular reflective wall so that all paths between the source and the thermopile situated in diametrally opposite positions are the same length. It includes a plurality of source—thermopile assemblies situated in diametrally opposite positions to render parallel the measurements and to improve sensitivity.

The optimum configuration corresponds to a geometry in which the lengths of the paths between the source and the detector show the least spread to ensure good linearity of the measurements and/or the length of the path is the longest, to ensure good sensitivity. The FIG. 3C configuration appears to be the optimum given the above criteria when only one source is used. The walls serving for collimation limit spread and lengthen the path travelled. When a plurality of sources can be used, the FIG. 4A geometry is also that which minimizes the spread on the paths travelled because of the collimators.

Figure 5A:
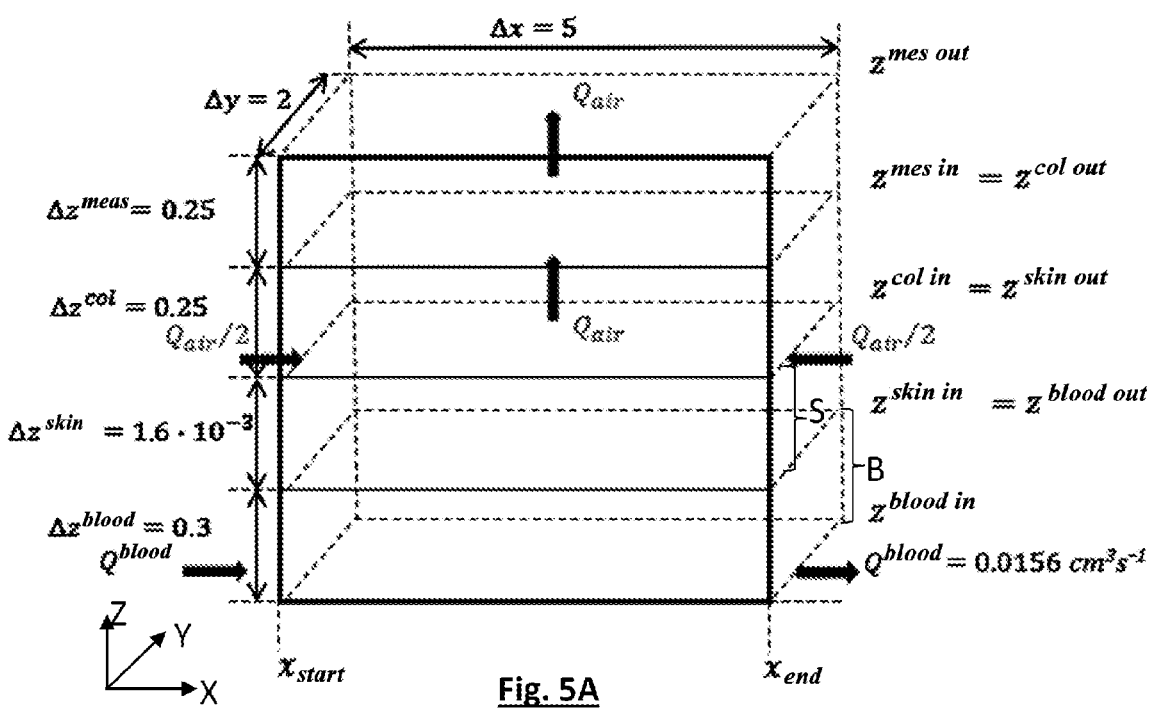
Figure 5B:
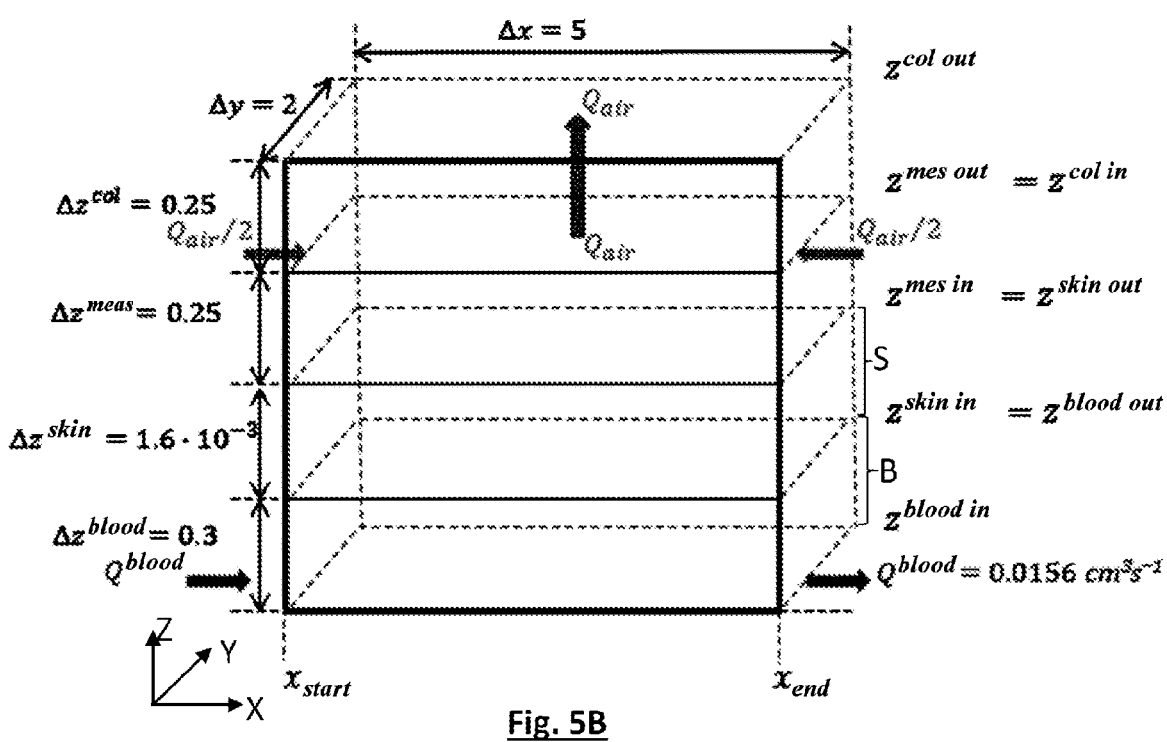
Figure 6A:
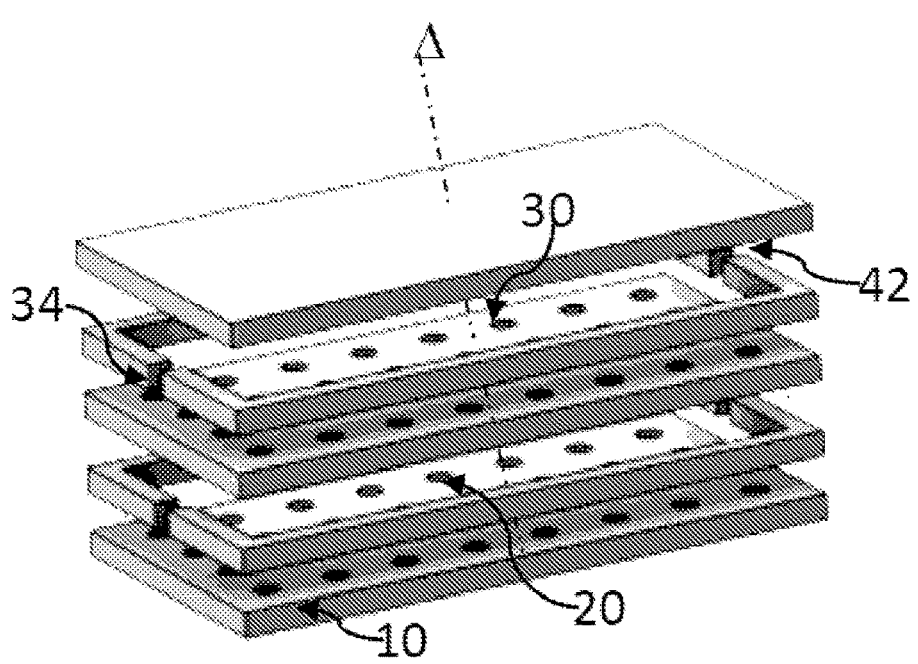
FIG. 6A is a diagram of a second embodiment.
Figure 6B:
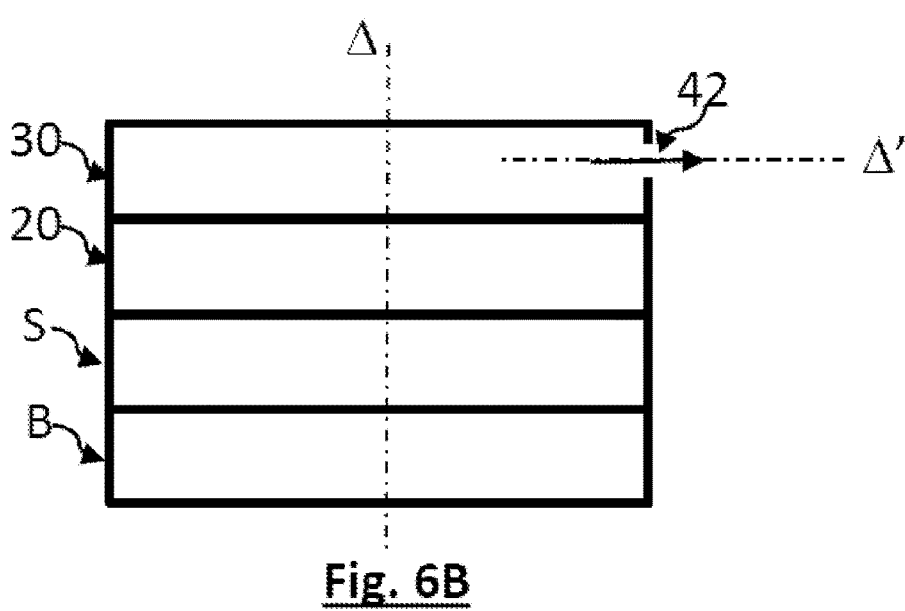
FIG. 6B is a diagram of a modeled second configuration corresponding to the second embodiment.

The inventors have simulated the detection performance of the detector as described in WO2020/249466 and of the detector according to the invention. FIGS. 5A, 5B and 5C are respectively diagrams of:

the device as described in WO2020/249466, representing the prior art;

a first embodiment "invention 1" of the device according to the invention;

a second embodiment "invention 2" of the device according to the invention, the device equally being represented in FIGS. 6A and 6B.

Regardless of the device, the blood occupies a blood compartment B between the coordinates $z^{blood\ in}$ and $z^{blood\ out}$ and its thickness is $\Delta z^{blood}$. The blood compartment B is covered by the skin S. The skin S extends between the coordinates $z^{skin\ in}$ and $z^{skin\ out}$ and its thickness is $\Delta z^{skin}$. $z^{skin\ in}=z^{blood\ out}$. The skin is covered by the device. The prior art device includes stacked collecting and measuring chambers. The collecting chamber extends between the coordinates $z^{col\ in}$ and $z^{col\ out}$ and its thickness is $\Delta z^{col}$. The measuring chamber extends between the coordinates $z^{meas\ in}$ and $z^{meas\ out}$ and its thickness is $\Delta z^{meas}$. In this geometry $z^{col\ in}=z^{skin\ out}$ and $z^{meas\ in}=z^{col\ out}$. According to the invention the device includes stacked measuring chamber 20 and collecting chamber 30. In this geometry $z^{meas\ in}=z^{skin\ out}$, $z^{col\ in}=z^{meas\ out}$.

The dimensioning parameters of the device are as follows:

Specification of the parameters:

length (along axis X) of blood compartment: $\Delta x^{blood}=\Delta x=5$ cm;

width (along axis Y) of blood compartment: $\Delta y^{blood}=\Delta y=2$ cm;

blood compartment height (along axis Z): $\Delta z^{blood}=0.3$ cm;

blood compartment area in contact with skin: $A^{blood}=10$ cm$^2$;

blood compartment volume: $V^{blood}=3$ cm$^3$;

Henry coefficient of carbon dioxide in blood: $H^{blood}=0.54$ diffusion coefficient of carbon dioxide in blood (water coefficient): $D^{blood}=2.2\ 10^{-5}$ cm$^2\cdot$s$^{-1}$ initial $CO_2$ concentration in blood: $C^{blood\ in}=1.0990$ µmol/cm3 blood flowrate: $Q^{blood}=0.0156$ cm$^3$s$^{-1}$, which corresponds to the following flow velocity:

transverse Flow velocity (along x):

$$u_x^{blood} = 0.0259\ \text{cm}.s^{-1}$$

skin compartment length (along axis X): $\Delta x^{skin}=\Delta x=5$ cm;

skin compartment width (along axis Y): $\Delta y^{skin}=\Delta y=2$ cm;

skin compartment height (along axis Z): $\Delta z^{skin}=16\ 10^{-4}$ cm;

area of skin in contact with device: $A^{skin}=10$ cm$^2$;

Henry coefficient of carbon dioxide in skin: $H^{skin}=1.6$;

diffusion coefficient of carbon dioxide in skin: $D^{skin}=1\ 10^{-7}$ cm$^2\cdot$s$^{-1}$ measuring chamber temperature: $T^{meas}=315.15$ K;

measuring chamber length (along axis X): $\Delta x^{meas}=\Delta x=5$ cm;

measuring chamber width (along axis Y): $\Delta y^{meas}=\Delta y=2$ cm;

measuring chamber height (along axis Z): $\Delta z^{meas}=0.25$ cm;

Henry coefficient of carbon dioxide in measuring chamber: $H^{meas}=H^{air}=1$ diffusion coefficient of carbon dioxide in measuring chamber: $D^{meas}=D^{air}=0.18$ cm$^2\cdot$s$^{-1}$ $CO_2$ concentration in incoming air, assuming a filter: $C^{air}=0$ convection air flowrate in measuring chamber:

prior art architecture: typically $Q^{air}=1$ ml/min: range of variation from 0.1 to 5 ml/min. This corresponds to the following flow velocity:

axial flow velocity (along z): typically $$u_z^{meas} = 1.67.10^{-3}\ \text{cm}.s^{-1}$$

convection air flowrate in measuring chamber of the invention: 0 ml/min axial flow velocity (along z):

$$u_z^{meas} = 0\ \text{cm}.s^{-1}$$

area of contact face between measuring chamber and collecting chamber: $A^{meas}=A^{col}=10$ cm$^2$;

collecting chamber temperature: $T^{col}$=315.15 K;

collecting chamber length (along axis X): $\Delta x^{col}$=$\Delta x$=5 cm;

collecting chamber width (along axis Y): $\Delta y^{col}$=$\Delta y$=2 cm;

collecting chamber height (along axis Z): $\Delta z^{col}$=0.25 cm;

Henry coefficient of carbon dioxide in collecting chamber: $H^{col}$=$H^{air}$=1 diffusion coefficient of carbon dioxide in collecting chamber: $D^{col}$=$D^{air}$=0.18 cm$^2 \cdot$s$^{-1}$ convection air flowrate in collecting chamber:

prior art architecture: typically $Q^{air}$=1 ml/min: range of variation from 0.1 to 5 ml/min. This corresponds to the following Flow velocity:

axial flow velocity (along z): typically $$u_z^{col} = 1.67.10^{-3} \text{ cm.s}^{-1}$$

convection air flowrate in collecting chamber of the invention: typically $Q^{air}$=1 ml/min: range of variation 0.1 to 5 ml/min. This corresponds to the following Flow velocities:

Invention 1: axial flow velocity (along z): typically $$u_z^{col} = 1.67.10^{-3}$$

$$\text{cm} \cdot \text{s}^{-1}$$

Invention 2: transverse flow velocity (along x):

$$u_x^{col} = 0.033 \text{ cm.s}^{-1}$$

The transparency factor $r_{meas\_transp}$ at the inlet of the measuring chamber is equal to 0.3. The transparency factor $r_{col\_transp}$ at the inlet of the collecting chamber is also equal to 0.3.

The objective of the geometry of the collecting chamber is to ensure circulation of air so that air travels all the area of exchange between the measuring chamber and the collecting chamber. This circulation of air occurs between the air admission openings and the air evacuation openings. If the pump is placed upstream of the collecting chamber relative to the air circulation circuit one or more tubes provide(s) the connection between the pump and the collecting chamber via the air admission openings. If the pump is placed downstream of the collecting chamber relative to the air circulation circuit one or more tubes provide(s) the connection between the collecting chamber and the pump.

In the case of transport with axial evacuation the evacuation hole or holes is or are placed in the ceiling of the collecting chamber. This evacuation could be centered if admission is effected at two or more opposed positions so that the air travels over all the area of exchange between the measuring chamber and the collecting chamber. It could also be off-center on a side opposite the air admission holes so that the air is able to travel all the area of exchange between the measuring chamber and the collecting chamber.

In the case of transport with transverse evacuation the evacuation hole or holes is or are situated on a lateral wall opposite the admission openings so that the air travels over all the area of exchange between the measuring chamber and the collecting chamber.

The admission and evacuation holes are sized so as to enable the required air flowrate $Q^{air}$ to be achieved.

In the case of a device with axial evacuation (FIG. 5A) the ceiling of the collecting chamber will advantageously have the shape of a funnel to guide the air toward the evacuation hole or holes.

An air admission or evacuation hole will typically have an area between 1 and 10 mm$^2$. This could represent a total admission or evacuation area up to 100 mm$^2$ if a plurality of holes are used in parallel.

Described next is the model describing the transport of the carbon dioxide from the blood to the evacuation holes of the collecting chamber via the skin and the measuring chamber. This model is based on collecting chamber and blood diffusion convection equations, convection—diffusion equations in the measuring chamber for the prior art configuration, and diffusion equations in the measuring chamber for the invention 1 and invention 2 configurations.

There is studied a dynamic model that is two-dimensional in terms of the spatial coordinates and time-dependent. The concentration variables depend on the spatial coordinates x and z, but are independent of the spatial coordinate y. These equations take account only of the spatial coordinates x and z and the time coordinate t.

Blood stage convection diffusion equation: valid for the three configurations (prior art, invention 1, invention 2)

$$\frac{\delta C_{CO_2}^{blood}}{\delta t} = -u_x^{blood} \frac{\delta C_{CO_2}^{blood}}{\delta x} + D^{blood} \left( \frac{\delta^2 C_{CO_2}^{blood}}{\delta x^2} + \frac{\delta^2 C_{CO_2}^{blood}}{\delta z^2} \right)$$

with:

$$u_x^{blood} = \frac{Q^{blood}}{\Delta y^{blood} * \Delta z^{blood}}$$

Edge Conditions:

$$\frac{\delta C_{CO_2}^{blood}}{\delta x}\left(x = x^{start}, z^{blood\ in} \leq z \leq z^{blood\ out}, t\right) = 0,$$

$$\frac{\delta C_{CO_2}^{blood}}{\delta z}\left(x^{start} \leq x \leq x^{end}, z = z^{blood\ in}, t\right) = 0,$$

$$\frac{\delta C_{CO_2}^{blood}}{\delta x}\left(x = x^{end}, z^{blood\ in} \leq x \leq x^{blood\ out}, t\right) = 0$$

$$C_{CO_2}^{blood}\left(x = x^{start}, z^{blood\ in} \leq z \leq z^{blood\ out}, t\right) = C_{CO_2}^{blood\ in}(t)$$

Blood Stage—Skin Stage Interface Conditions:

for:

$$x^{start} \leq x \leq x^{end}$$

$$C_{CO_2}^{blood}\left(x, z = z^{blood\ out}, t\right) \frac{H^{blood}}{H^{skin}} C_{CO_2}^{skin}\left(x, z = z^{skin\ in}, t\right)$$

$$D^{skin} \frac{\delta C_{CO_2}^{skin}}{\delta z}\left(x, z = z^{skin\ in}, t\right) = D^{blood} \frac{\delta C_{CO_2}^{blood}}{\delta z}\left(x, z = z^{blood\ out}, t\right)$$

Skin Diffusion Equation: Valid for the Three Configurations (Prior Art, Invention 1, Invention 2)

$$\frac{\delta C_{CO_2}^{skin}}{\delta t} = D^{skin}\left(\frac{\delta^2 C_{CO_2}^{skin}}{\delta x^2} + \frac{\delta^2 C_{CO_2}^{skin}}{\delta z^2}\right)$$

Edge Conditions:

$$\frac{\delta C_{CO_2}^{skin}}{\delta x}\left(x = x^{start}, z^{skin\ in} \le z \le z^{skin\ out}, t\right) = 0,$$

$$\frac{\delta C_{CO_2}^{skin}}{\delta x}\left(x = x^{end}, z^{skin\ in} \le z \le z^{skin\ out}, t\right) = 0$$

Collecting Chamber Convection Diffusion Equation: Prior Art Configuration:

$$\frac{\delta C_{CO_2}^{col}}{\delta t} = -u_Z^{col}\frac{\delta C_{CO_2}^{col}}{\delta z} + D^{air}\left(\frac{\delta^2 C_{CO_2}^{col}}{\delta x^2} + \frac{\delta^2 C_{CO_2}^{col}}{\delta z^2}\right)$$

with $$u_z^{col} = \frac{Q^{air}}{\Delta x^{col} * \Delta y^{col}}$$

Edge Conditions $$\frac{\delta C_{CO_2}^{col}}{\delta x}\left(x = x^{start}, z^{col\ in} \le z \le z^{col\ out}, t\right) = 0,$$

$$\frac{\delta C_{CO_2}^{col}}{\delta x}\left(x = x^{end}, \left(x = x^{start}, z^{col\ in} \le z \le z^{col\ out}\right), t\right) = 0$$

$$C_{CO_2}^{col}\left(x^{start} \le x \le x^{end}, z = z^{col\ in}, t\right) = C_{CO_2}^{air\ col\ in}(t)$$

It is assumed that $$C_{CO_2}^{air\ col\ in}(t)$$

is a constant: the concentration of CO2 introduced via the lateral walls is constant.

Skin—Collecting Chamber Interface Conditions: for:

$$x^{start} \le x \le x^{end}$$

$$C_{CO_2}^{skin}\left(x, z = z^{skin\ out}, t\right) = H^{skin} C_{CO_2}^{col}\left(x, z = z^{col\ in}, t\right)$$

$$r_{transpacol} D^{skin}\frac{\delta C_{CO_2}^{skin}}{\delta z}\left(x, z = z^{skin\ out}, t\right) = D^{air}\frac{\delta C_{CO_2}^{col}}{\delta z}\left(x, z = z^{col\ in}, t\right)$$

Invention 1: the collecting chamber is above the measuring chamber, the air outlet is axial in direction z, the transport equations are the same but the conditions at the interfaces are different:

$$\frac{\delta C_{CO_2}^{col}}{\delta t} = -u_z^{col}\frac{\delta C_{CO_2}^{col}}{\delta z} + D^{air}\left(\frac{\delta^2 C_{CO_2}^{col}}{\delta x^2} + \frac{\delta^2 C_{CO_2}^{col}}{\delta z^2}\right)$$

$$C_{CO_2}^{col}\left(x^{start} \le x \le x^{end}, z = z^{col\ in}, t\right) = C_{CO_2}^{air\ col\ in}(t)$$

with $$u_z^{col} = \frac{Q^{air}}{\Delta x^{col} * \Delta y^{col}}$$

Edge Conditions $$\frac{\delta C_{CO_2}^{col}}{\delta x}\left(x = x^{start}, z^{col\ in} \le z \le z^{col\ out}, t\right) = 0,$$

$$\frac{\delta C_{CO_2}^{col}}{\delta x}\left(x = x^{end}, z^{col\ in} \le z \le z^{col\ out}, t\right) = 0,$$

$$\frac{\delta C_{CO_2}^{col}}{\delta z}\left(x^{start} \le x \le x^{end}, z = z^{col\ out}, t\right) = 0$$

Measuring Chamber—Collecting Chamber Interface Conditions: for:

$$x^{start} \le x \le x^{end}$$

$$r_{transpa\_col}\frac{\delta C_{CO_2}^{meas}}{\delta z}\left(x, z = z^{meas\ out}, t\right) = \frac{\delta C_{CO_2}^{col}}{\delta z}\left(x, z = z^{col\ in}, t\right)$$

Invention 2: the collecting chamber is above the measuring chamber, the air outlet is transverse in direction x, the transport equations change in terms of the direction of the flow of air, the conditions at the interfaces are different:

$$\frac{\delta C_{CO_2}^{col}}{\delta t} = -u_x^{col}\frac{\delta C_{CO_2}^{col}}{\delta z} + D^{air}\left(\frac{\delta^2 C_{CO_2}^{col}}{\delta x^2} + \frac{\delta^2 C_{CO_2}^{col}}{\delta z^2}\right)$$

$$C^{col}\left(x = x^{start}, z^{col\ in} \le z < z^{col\ out}, t\right) = C_{CO_2}^{air\ col\ in}(t)$$

with $$u_x^{col} = \frac{Q^{air}}{\Delta z^{col} * \Delta y^{col}}$$

Edge Conditions $$\frac{\delta C_{CO_2}^{col}}{\delta x}\left(x = x^{start}, z^{col\ in} \le z \le z^{col\ out}, t\right) = 0,$$

$$\frac{\delta C_{CO_2}^{col}}{\delta x}\left(x = x^{end}, z^{col\ in} \le z \le z^{col\ out}, t\right) = 0,$$

$$\frac{\delta C_{CO_2}^{col}}{\delta z}\left(x^{start} \le x \le x^{end}, z = z^{col\ out}, t\right) = 0$$

Measuring Chamber—Collecting Chamber Interface Conditions:

for:

$$x^{start} \leq x \leq x^{end}$$

$$C_{CO_2}^{meas}(x, z = z^{meas\ out}, t) = C_{CO_2}^{col}(x, z = z^{col\ in}, t)$$

$$r_{transpa\_col} \frac{\delta C_{CO_2}^{meas}}{\delta z}(x, z = z^{meas\ out}, t) = \frac{\delta C_{CO_2}^{col}}{\delta z}(x, z = z^{col\ in}, t)$$

Measuring Chamber Convection Diffusion Equation Prior Art:

$$\frac{\delta C_{CO_2}^{meas}}{\delta t} = -u_z^{meas} \frac{\delta C_{CO_2}^{meas}}{\delta z} + D^{air}\left(\frac{\delta^2 C_{CO_2}^{meas}}{\delta x^2} + \frac{\delta^2 C_{CO_2}^{meas}}{\delta z^2}\right)$$

with $$u_z^{meas} = \frac{Q^{air}}{\Delta x^{meas} * \Delta y^{meas}}$$

Edge Conditions $$\frac{\delta C_{CO_2}^{meas}}{\delta x}(x = x^{start}, z^{meas\ in} \leq z \leq z^{meas\ out}, t) = 0,$$

$$\frac{\delta C_{CO_2}^{meas}}{\delta x}(x = x^{end}, z^{meas\ in} \leq z \leq z^{meas\ out}, t) = 0,$$

$$\frac{\delta C_{CO_2}^{meas}}{\delta z}(x^{start} \leq x \leq x^{end}, z = z^{meas\ out}, t) = 0$$

Collecting Chamber—Measuring Chamber Interface Conditions:

for $$x^{start} \leq x \leq x^{end}$$

$$C_{CO_2}^{col}(x, z = z^{col\ out}, t) = C_{CO_2}^{meas}(x, z = z^{meas\ in}, t)$$

$$r_{meas\_transp} \frac{\delta C_{CO_2}^{col}}{\delta z}(x, z = z^{col\ out}, t) = \frac{\delta C_{CO_2}^{meas}}{\delta z}(x, z = z^{meas\ in}, t)$$

Inventions 1 and 2: the measuring chamber is in contact with the skin:

$$\frac{\delta C_{CO_2}^{meas}}{\delta t} = D^{air}\left(\frac{\delta^2 C_{CO_2}^{meas}}{\delta x^2} + \frac{\delta^2 C_{CO_2}^{meas}}{\delta z^2}\right)$$

Edge Conditions $$\frac{\delta C_{CO_2}^{meas}}{\delta x}(x = x^{start}, z^{meas\ in} \leq z \leq z^{meas\ out}, t) = 0,$$

$$\frac{\delta C_{CO_2}^{meas}}{\delta x}(x = x^{end}, z^{meas\ in} \leq z \leq z^{meas\ out}, t) = 0$$

Skin—Measuring Chamber Interface Conditions:

for:

$$x^{start} \leq x \leq x^{end}$$

$$C_{CO_2}^{skin}(x, z = z^{skin\ out}, t) = H^{skin} C_{CO_2}^{meas}(x, z = z^{meas\ in}, t)$$

$$r_{meas\_transp} D^{skin} \frac{\delta C_{CO_2}^{skin}}{\delta z}(x, z = z^{skin\ out}, t) = D^{air} \frac{\delta C_{CO_2}^{meas}}{\delta z}(x, z = z^{meas\ in}, t)$$

For each configuration modeling has been carried out using software simulating the transport of the carbon dioxide from the blood through the skin to the measuring and collecting chambers.

In the prior art architecture the transport of the gaseous $CO_2$ is described by an equation of convection in the blood compartment, in the collecting chamber compartment and in the measuring chamber compartment and by a diffusion equation in the skin. In the architecture of the device according to the invention the transport is described by a diffusion equation in the skin and in the measuring chamber compartment and by a convection diffusion equation in the blood compartment and in the collecting chamber compartment.

In this two-dimensional model the measured signal $$\overline{C_{CO_2}^{meas}}(t)$$

is calculated at the output of the measuring cell by taking the mean value of the concentration according to the variable x:

$$\overline{C_{CO_2}^{meas}}(t) = \frac{1}{x^{end} - x^{start}} \int_{x^{start}}^{x^{end}} C_{CO_2}^{meas}(x, z = z^{meas\ out}, t) dx$$

Two parameters representative of the performance of each architecture have been estimated:

The rise time $\Delta t$, which corresponds to the time necessary to pass between 10% and 90% of the amplitude of variation of the concentration measured in the measuring chamber following a $CO_2$ partial pressure variation forming a step change between a low value and a high value. The rise time $\Delta t$ is schematically represented in FIG. 5C: curve a) is a schematic representation of the response to the step change if the measurement were instantaneous while curve b) corresponds to the response of the gas sensor 23 allowing for the kinetics of the transport of the carbon dioxide. The responses have been normalized in FIG. 5C so that the low value corresponds to 0 and the high value to 1.

Figures 5D, 5E, 5F:
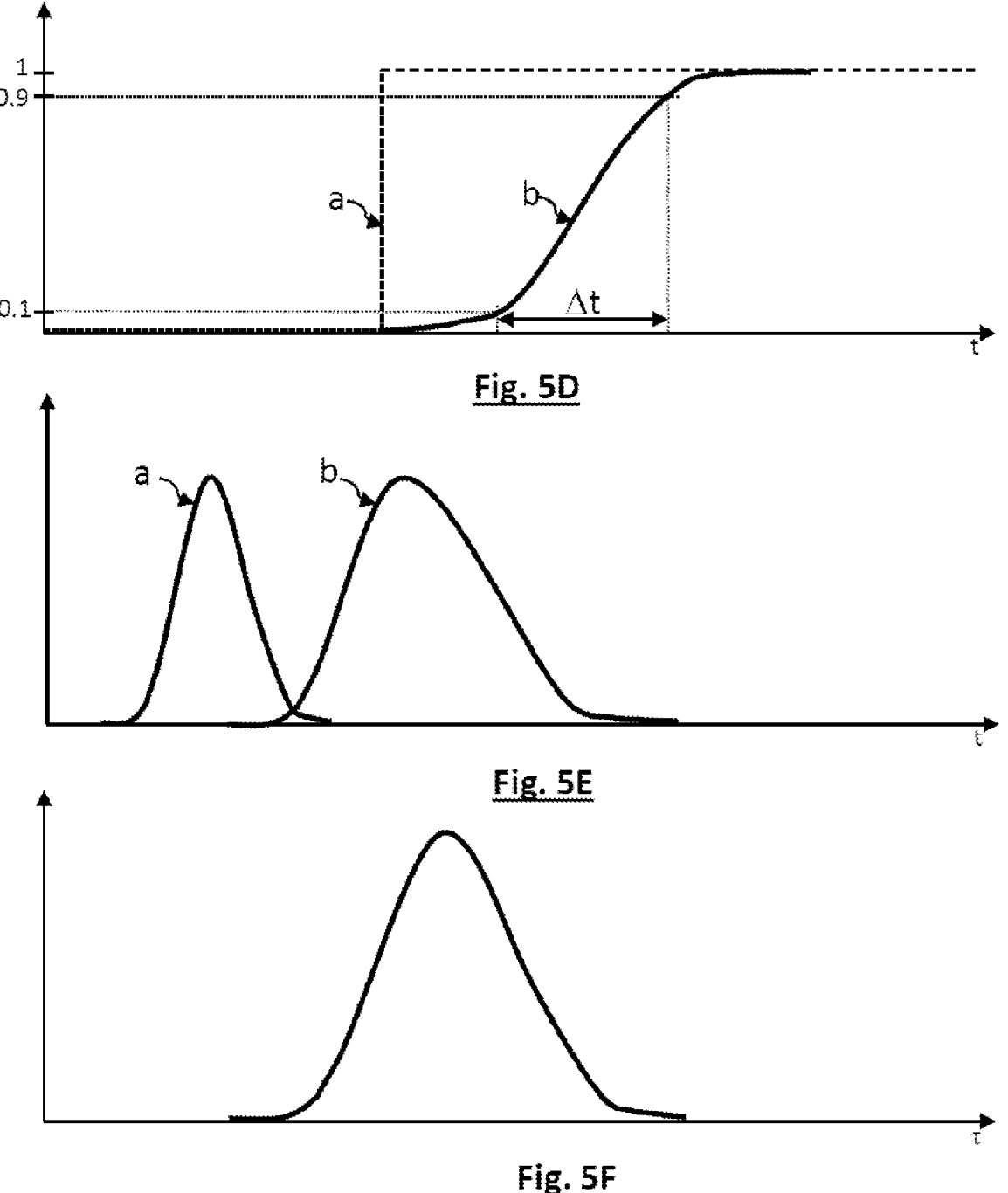
FIG. 5D depicts determination of a response time.
FIG. 5E depicts a simulated $CO_2$ concentration in the blood pulse and a $CO_2$ concentration pulse as measured by the gas sensor of the device.
FIG. 5F depicts determination of a delay time based on temporal intercorrelation of the curves represented in FIG. 5E.

The delay time $\tau$ that corresponds to a maximum of the intercorrelation function between a concentration pulse in the blood, represented for example by a bell-shaped spline function as represented in curve a in FIG. 5E and the concentration pulse measured by the gas sensor 23. The delay time is similar to a time for propagation of the carbon dioxide between the blood, the skin and the measuring chamber. In FIG. 5D curve a) and curve b) respectively and schematically represent the concentration pulse in the blood and the concentration pulse measured by the gas sensor. In this diagram the amplitudes of the two pulses have been normalized to the same value. FIG. 5E schematically represents an intercorrelation function between curves a) and b) in FIG.

5D. The delay time τ retained is that corresponding to the maximum of the intercorrelation function.

The intercorrelation function $\Gamma yz(\tau)$ between a signal y(t) and a signal z(t) is of the following type:

$$\Gamma yz(\tau) = \frac{\lim\limits_{T\to\infty} \frac{1}{2T}\int_{-T}^{T}\int (y(t)-\mu_y)(z(t-\tau)-\mu_Z)dt}{\sigma_y\sigma_z}$$

where:

$$\mu_y = \lim\limits_{T\to\infty} \frac{1}{2T}\int_{-T}^{T} y(t)dt$$

$$\mu_z = \lim\limits_{T\to\infty} \frac{1}{2T}\int_{-T}^{T} z(t)dt$$

$$\sigma_y = \lim\limits_{T\to\infty} \sqrt{\frac{1}{2T}\int_{-T}^{T} (y(t)-\mu_y)^2 dt}$$

$$\sigma_z = \lim\limits_{T\to\infty} \sqrt{\frac{1}{2T}\int_{-T}^{T} (z(t)-\mu_z)^2 dt}$$

where y(t) corresponds to the concentration pulse in the blood and z(t) corresponds to the concentration pulse measured by the gas sensor 23 in the measuring chamber.

There has been modelled the evolution over time of the $CO_2$ concentration measured by the measuring chamber so as to determine the rise time and the delay time, or overall delay. Between one modelling and the next, the air flowrate imposed by the pump has been varied between 1 mL/min and 5 mL/min. Table 1 shows for each flowrate the rise time and the overall delay (or delay time) simulated for different flowrate values of the pump 41.

TABLE 1

| Q_air (ml/min) | Parameter studied | Prior art | Invention |
|---|---|---|---|
| 0.1 | Rise time (s) | 17152.8 | 7258.1 |
|  | Overall delay (s) | 445.1 | 376.5 |
| 0.2 | Rise time (s) | 9229.8 | 3769.4 |
|  | Overall delay (s) | 396.2 | 324.7 |
| 0.5 | Rise time (s) | 3922.6 | 1606 |
|  | Overall delay (s) | 328.5 | 257.1 |
| 1 | Rise time (s) | 2051.8 | 879.3 |
|  | Overall delay (s) | 277.3 | 208.4 |
| 2 | Rise time (s) | 1100.9 | 528.8 |
|  | Overall delay (s) | 227.4 | 163.3 |
| 3 | Rise time (s) | 785.9 | 420.5 |
|  | Overall delay (s) | 199.6 | 139.3 |
| 4 | Rise time (s) | 631.9 | 369.5 |
|  | Overall delay (s) | 180.5 | 123.5 |
| 5 | Rise time (s) | 542.2 | 340.4 |
|  | Overall delay (s) | 166.3 | 112 |

It is seen that performance in terms of rise time and overall delay are better with the device according to the invention than with the device having the geometry described in the prior art.

Table 2 shows the concentrations and partial pressures of $CO_2$ measured by the measuring chamber where the concentration of $CO_2$ in the blood corresponds to a partial pressure of 40 mm of mercury.

TABLE 2

| Q_air (ml/min) | Parameter studied | Prior art | Invention 1 |
|---|---|---|---|
| 0.1 | Concentration (μmol/cm3) | 0.26486 | 0.0874 |
|  | Partial pressure (mmHg) | 5.2055 | 1.7185 |
| 0.2 | Concentration (μmol/cm3) | 0.14164 | 0.0447 |
|  | Partial pressure (mmHg) | 2.7839 | 0.8783 |
| 0.5 | Concentration (μmol/cm3) | 0.05913 | 0.01813 |
|  | Partial pressure (mmHg) | 1.1621 | 0.3563 |
| 1 | Concentration (μmol/cm3) | 0.029999 | 0.0091146 |
|  | Partial pressure (mmHg) | 0.5896 | 0.17914 |
| 2 | Concentration (μmol/cm3) | 0.015111 | 0.004578 |
|  | Partial pressure (mmHg) | 0.29699 | 0.089976 |
| 3 | Concentration (μmol/cm3) | 0.010099 | 0.0030613 |
|  | Partial pressure (mmHg) | 0.19848 | 0.060167 |
| 4 | Concentration (μmol/cm3) | 0.0075836 | 0.0023021 |
|  | Partial pressure (mmHg) | 0.14905 | 0.045246 |
| 5 | Concentration (μmol/cm3) | 0.0060714 | 0.0018463 |
|  | Partial pressure (mmHg) | 0.11933 | 0.036288 |

Table 3 shows a comparison of the values of the rise time and the overall delay using the first embodiment (invention 1) and the second embodiment (invention 2). Note that the second embodiment, in which the air outlet is perpendicular to the central axis, is more favorable in terms of rise time and overall delay. However, the concentrations and partial pressures measured for a concentration in the blood equivalent to a partial pressure of 40 mm of mercury are less with the second embodiment than with the first embodiment (table 4)

TABLE 3

| Q_air (ml/min) | Parameter studied | Invention 1 | Invention 2 |
|---|---|---|---|
| 0.1 | Rise time (s) | 7258.1 | 4434.9 |
|  | Overall delay (s) | 376.5 | 336.8 |
| 0.2 | Rise time (s) | 3769.4 | 2288.1 |
|  | Overall delay (s) | 324.7 | 283.7 |
| 0.5 | Rise time (s) | 1606 | 980.7 |
|  | Overall delay (s) | 257.1 | 214.4 |
| 1 | Rise time (s) | 879.3 | 556.6 |
|  | Overall delay (s) | 208.4 | 164 |
| 2 | Rise time (s) | 528.8 | 363.7 |
|  | Overall delay (s) | 163.3 | 117.8 |
| 3 | Rise time (s) | 420.5 | 306.3 |
|  | Overall delay (s) | 139.3 | 94.2 |
| 4 | Rise time (s) | 369.5 | 280.1 |
|  | Overall delay (s) | 123.5 | 79.4 |
| 5 | Rise time (s) | 340.4 | 265.7 |
|  | Overall delay (s) | 112 | 69.4 |

TABLE 4

| Q_air (ml/min) | Parameter studied | Invention 1 | Invention 2 |
|---|---|---|---|
| 0.1 | Concentration (μmol/cm3) | 0.0874 | 0.052896 |
|  | Partial pressure (mmHg) | 1.7185 | 1.0396 |
| 0.2 | Concentration (μmol/cm3) | 0.0447 | 0.02657 |
|  | Partial pressure (mmHg) | 0.8783 | 0.52217 |
| 0.5 | Concentration (μmol/cm3) | 0.01813 | 0.010463 |
|  | Partial pressure (mmHg) | 0.3563 | 0.20563 |
| 1 | Concentration (μmol/cm3) | 0.0091146 | 0.0050767 |
|  | Partial pressure (mmHg) | 0.17914 | 0.099777 |
| 2 | Concentration (μmol/cm3) | 0.004578 | 0.0024238 |
|  | Partial pressure (mmHg) | 0.089976 | 0.047637 |
| 3 | Concentration (μmol/cm3) | 0.0030613 | 0.0015655 |
|  | Partial pressure (mmHg) | 0.060167 | 0.030769 |
| 4 | Concentration (μmol/cm3) | 0.0023021 | 0.0011484 |
|  | Partial pressure (mmHg) | 0.045246 | 0.02257 |
| 5 | Concentration (μmol/cm3) | 0.0018463 | 0.00090425 |
|  | Partial pressure (mmHg) | 0.036288 | 0.017772 |

Although described with reference to a measurement of transcutaneous $CO_2$, the invention may be employed in other applications, so as to measure a gas emitted by a solid or liquid medium. The medium may in particular be:

a plant, for example a fruit, to monitor the ripening process;

slurry, to monitor the emission of gas, for example methane;

a biological organism or microorganism culture medium;

water, for example fresh water or sea water, for example to monitor or to regulate the gas concentration;

soil, so as study the respiration thereof;

a liquid medium intended for breeding fish.

The invention claimed is:

1. A measuring device configured to be disposed against a medium, the device extending between a contact face configured to be applied facing the medium and a distal end, the device including a lateral wall extending between the contact face and the distal end, the device comprising:

at a level of the contact face, an admission opening configured to collect a gas of interest emitted through the medium, the admission opening being through the contact face;

a measuring chamber including a gas sensor, the gas sensor being configured to measure a concentration of the gas of interest flowing through the measuring chamber, the measuring chamber being delimited by the lateral wall and disposed above the contact face;

a collecting chamber connected to the measuring chamber by an opening, the collecting chamber including a lateral opening through the lateral face so as to admit a vector gas into the collecting chamber, the collecting chamber being delimited by the lateral wall and disposed above the measuring chamber such that the measuring chamber is disposed between the contact face and the collecting chamber;

a pump configured to drive the vector gas admitted through the lateral opening across the collecting chamber to an evacuation opening; and collecting openings, distributed across a collecting plate, said collecting plate separating the measuring chamber and the collecting chamber, so that driving the vector gas through the collecting chamber induces a reduction or a partial pressure of the gas of interest in the collecting chamber, thereby inducing diffusion of the gas of interest from the contact face to the collecting chamber via the measuring chamber, through the collecting openings.

2. The device as claimed in claim 1, further comprising a heat source configured to heat the contact face to a temperature greater than 37° C.

3. The device as claimed in claim 1, wherein the evacuation opening is oriented about an evacuation axis perpendicular or perpendicular to within 30° to the contact face, the collecting chamber opening into the evacuation opening.

4. The device as claimed in claim 1, wherein the evacuation opening is through the lateral wall of the collecting chamber.

5. The device as claimed in claim 1, wherein the gas sensor of the measuring chamber is disposed at a distance less than 8 mm from the contact face.

6. The device as claimed in claim 1, wherein the gas sensor is an optical sensor including an infrared source configured to emit infrared light and a photodetector, the measuring chamber being such that the gas of interest flows in the measuring chamber between the infrared source of and the photodetector in a flow direction perpendicular or perpendicular ±30° to the contact face.

7. The device as claimed in claim 6 wherein the infrared source is configured to produce a flat light beam parallel or parallel to within ±30° to the contact face.

8. The device as claimed in claim 7, wherein a thickness of the flat light beam in a direction of a transverse axis perpendicular to the contact face is less than 5 mm.

9. The device as claimed in claim 8, wherein the measuring chamber includes two walls parallel to the contact face, each wall being reflective to the infrared light emitted by the infrared source, the walls delimiting the flat light beam in which the infrared light propagates between the infrared source and the photodetector.

10. The device as claimed in claim 9, wherein a reflecting wall forms the contact face.

11. The device as claimed in claim 10, wherein the reflecting wall nearest the contact face is configured to be heated so as to heat the medium.

12. The device as claimed in claim 9, wherein:

each reflecting wall includes transverse baffles;

each transverse baffle of a reflective wall extends toward an opposite reflective wall;

a gap is formed between each transverse baffle and the reflective wall opposite it the transverse baffle;

a transverse baffle of a reflective wall extends between two transverse baffles of the opposite reflective wall; and se that the light emitted by the light source propagates between the successive transverse baffles before reaching the detector.

13. The device as claimed in claim 1, wherein an air flowrate of the pump is between 0.1 and 10 mL/min.

14. A method of estimating a concentration of a gas of interest in a medium using a device as claimed in claim 1, the device being applied so that the contact face is disposed facing the medium, the pump being activated, the method comprising:

a) estimating a gas of interest concentration in the measuring chamber; and b) from the gas of interest concentration in the measuring chamber resulting from step a) estimating the partial pressure of the gas of interest given off by the medium.

15. The method as claimed in claim 14, wherein the medium is the skin of a user, the skin extending over a blood vessel, and step b) includes:

(i) on the basis of the gas of interest concentration in the measuring chamber resulting from step a) estimating a transcutaneous gas of interest concentration;

(ii) estimating a concentration or partial pressure of the gas of interest dissolved in medium on the basis of the transcutaneous gas of interest concentration resulting from sub-step (i).

16. The method as claimed in claim 14, wherein the medium to be analyzed is a solid or liquid medium.

17. The method as claimed in in claim 14, wherein the vector gas is air.

18. The device of claim 1, wherein the collection openings are distributed across a cross section greater than 1 cm$^2$.

*   *   *   *   *